United States Patent
Towsley

Patent Number: 5,840,051
Date of Patent: Nov. 24, 1998

[54] FLEXIBLE BACK, NECK AND SHOULDER BRACE

[76] Inventor: Harold E. Towsley, 1821 Greenstone Dr., New Haven, Ind. 46774

[21] Appl. No.: 912,728

[22] Filed: Aug. 18, 1997

Related U.S. Application Data

[63] Continuation-in-part of Ser. No. 519,082, Aug. 24, 1995, Pat. No. 5,669,873.

[51] Int. Cl.⁶ .................................................. A61F 5/00
[52] U.S. Cl. .................................... 602/19; 602/16; 2/44
[58] Field of Search ...................... 602/19, 16; 128/846, 128/870; 2/2, 92, 44, 45

[56] References Cited

U.S. PATENT DOCUMENTS

| | | | |
|---|---|---|---|
| 4,541,419 | 9/1985 | Osawa | 602/19 |
| 5,140,995 | 8/1992 | Uhl | 128/846 |
| 5,400,801 | 3/1995 | Archer, III | 128/846 |
| 5,669,873 | 9/1997 | Towsley | 602/26 |

*Primary Examiner*—Linda C. M. Dvorak
*Attorney, Agent, or Firm*—Roger M. Rickert

[57] ABSTRACT

An orthopedic brace for spinal applications is formed from a plurality of relatively rigid hollowed-out parallelepiped portions adjacent pairs of which are joined along a relatively thin web of flexible material common to the two portions to provide pivotal motion between the two adjacent portions. Relative pivotal movement between the two adjacent portions is selectively restricted by an elongated threaded rod which is pivotably affixed at one end to one of the parallelepiped portions and extends through a portion of the other parallelepiped portion with a nut threadedly engaging the rod for adjustment therealong to selectively pull the other parallelepiped portion angularly toward the one parallelepiped portion. The nut engages a resilient washer to provide a limited yielding between the portions. The number of such portions joined together is arbitrary. In the preferred back brace form, there are numerous parallelepiped portions each joined to another to form a pair by a relatively thin web and each pair having a threaded rod and nut for selectively restricting pivotal movement between the portions of the pair. In a preferred form, the brace is for exterior posterior application to a human patient by a pair of shoulder straps, a waist strap, and forehead and chin straps.

22 Claims, 3 Drawing Sheets

5,840,051

FLEXIBLE BACK, NECK AND SHOULDER BRACE

CROSS-REFERENCE TO RELATED APPLICATION

This application is a continuation-in-part of my application Ser. No. 08/519,082 filed Aug. 24, 1995, now U.S. Pat. No. 5,669,873 and entitled FLEXIBLE KNEE AND LEG BRACE.

SUMMARY OF THE INVENTION

The present invention relates generally to orthotic appliances of the type employed to arrest or correct deformation of a body part or to otherwise support, supplement or immobilize weakened joints. In particular, the present invention relates to a spinal column brace suitable for correcting certain spinal column deformities, delaying or avoiding back surgery, substituting for a body cast after back surgery, or otherwise supplementing the spinal column's function.

Such orthotic devices are generally quite complex, yet limited in their range of adjustments and hence quite individualized in their applicability. These problems are exaggerated when the orthosis is adapted to complexly articulated parts of the body such as the spine.

Many such spinal column braces completely surround a substantial portion of the patient's torso making them very uncomfortable in warm weather and rendering bathing nearly impossible. For example, see U.S. Pat. Nos. 4,202,327; 4,285,336; 4,648,390; and 4,688,558. Others, such as shown in U.S. Pat. No. 3,945,376, are more nearly skeletal structures. This last mentioned patented device does supply both head and back support, but still surrounds the patient's torso and is extremely awkward to put on and remove.

Among the several objects of the present invention may be noted the provision of an entirely posterior, exterior spinal column brace; the provision of a highly individualizable orthopedic brace for arresting or correcting kyphosis, lordosis or other spinal abnormalities; the provision of an externally applied (non-invasive) spinal appliance which may be easily and repeatedly modified to urge certain body parts in selected directions and by selected amounts relative to other body parts; the provision of an external artificial spinal column which may be used to reinforce or apply corrective forces to a defective or deteriorating internal spinal column; and the provision of a unique back and neck brace. These as well as other objects and advantageous features of the present invention will be in part apparent and in part pointed out hereinafter.

In general, an externally applied non-invasive spinal column orthopedic appliance includes a plurality of generally vertically aligned rigid members certain pairs of which are pivotably coupled together for relative angular movement about one or more horizontal axes. There are a plurality of similar transversely aligned pivotably coupled rigid members. There are arrangements for selectively restricting the angular movement of the pivotably coupled rigid members. One or more resilient pads removably affixed to each of the rigid members are interposed between the rigid members and the wearer's back, hip and shoulders. Optionally, the appliance also includes a vertically adjustable padded head rest with straps for encircling a wearer's chin and forehead having a similar pivotable coupling for relative angular movement about another horizontal axis.

Also in general and in one form of the invention, an orthopedic appliance for posterior application to a human has a first plurality of longitudinally extending articulated segments which are positionable to extend generally along the human spine. Adjacent pairs of the first plurality of segments are pivotably joined for relative angular movement about a first set of pairwise parallel bending moment axes. There is a second plurality of transversely extending articulated segments pivotably joined for relative angular movement about a second set of pairwise parallel bending moment axes which axes extend generally orthogonal to said first set of bending moment axes. A foundation bracket and waistband strap are fastened to a lower end one of said first plurality of segments for encircling a human's waist, and a pair of shoulder straps are fastened to an outermost pair of the second plurality of segments for encircling each of a human's arms near the torso.

BRIEF DESCRIPTION OF THE DRAWING

Corresponding reference characters indicate corresponding parts throughout the several views of the drawing.

Figure 1:
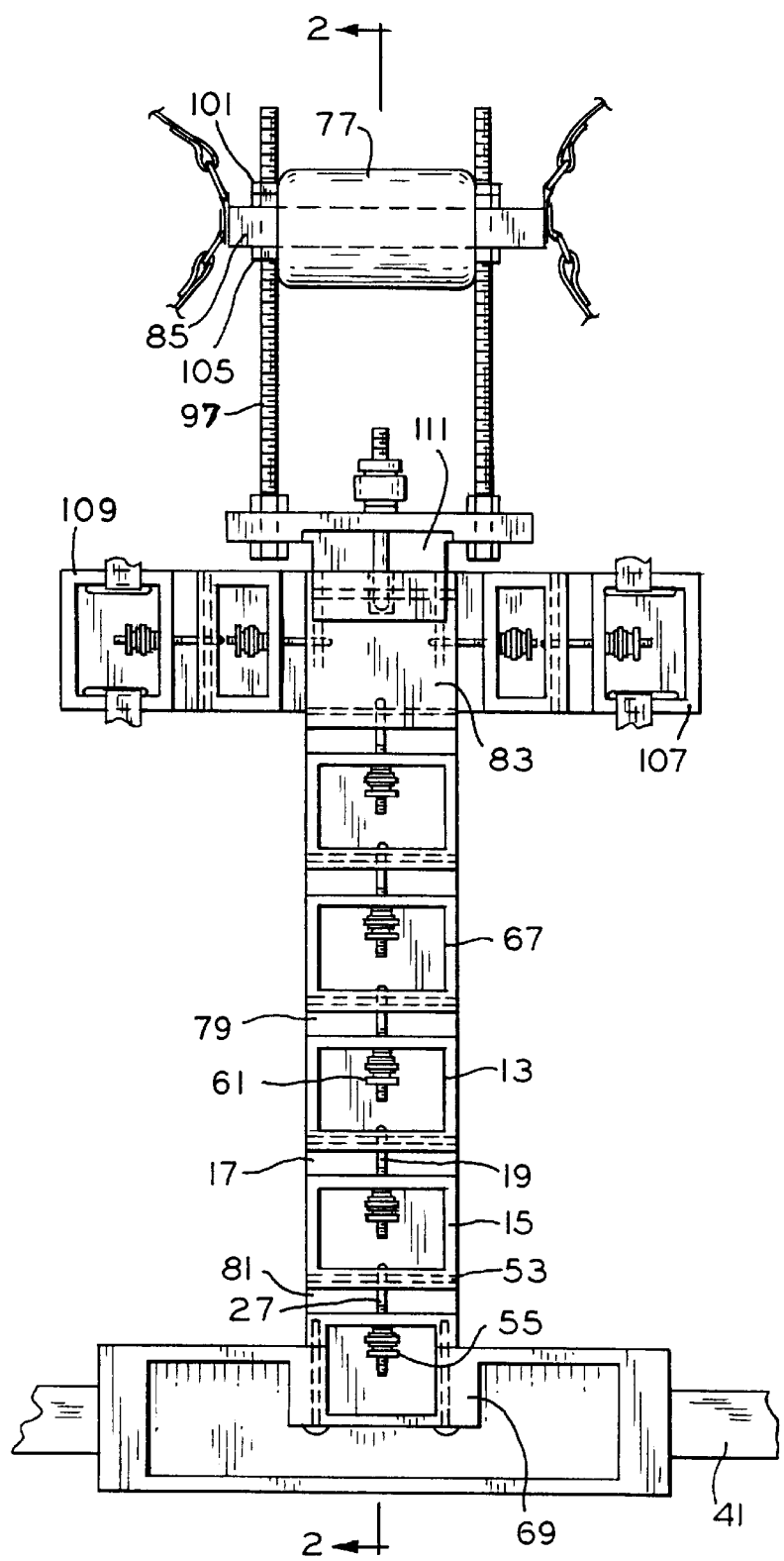
FIG. 1 is a front elevation view of the back brace of the present invention.

The exemplifications set out herein illustrate a preferred embodiment of the invention in one form thereof and such exemplifications are not to be construed as limiting the scope of the disclosure or the scope of the invention in any manner.

DESCRIPTION OF THE PREFERRED EMBODIMENT

The drawing generally illustrates an externally applied non-invasive spinal column appliance or brace which is adapted to span a plurality of human vertebrae between the padded head rest 85 and the padded hip foundation bracket segment 69. The brace is formed from a plurality of generally longitudinally aligned rigid members such as 13, 15 and 69 which are pivotably coupled together by interconnecting webs such as 17, 79 and 81 for relative angular movement about a bending moment axis which is generally parallel to and fairly close to the transverse pin 21. The angular movement of each pivotably coupled pair such as 13 and 15 about the bending moment axis may be selectively restricted by the threaded rods such as 19 which has an eye for engaging the transverse pin 21 of one of the adjacent members and a washer such as 33 for engaging the other of the adjacent rigid members so that tightening of the nuts such as 25 or 61 functions to pull the adjacent rigid members angularly toward one another. A number of straps are included for encircling portions of a patient's body to secure the rigid members to the body and to transfer bending moment forces to the patient's spinal column. A first strap 41 is designed to encircle the patient's waist and is attached to the lowermost one of the rigid members, foundation bracket 69. The waistband and rigid foundation bracket 69 serve to anchor the brace at the waist to provide one of the main locations from which a bending moment may be applied to the spinal column and prevent separation of the vertical portion of the brace from the patient's back. Another strap such as 47 or 49, either of which is adaptable to encircle a patient's head, is attached to the uppermost one of the rigid members, headrest 85. In the preferred embodiment, both a chin strap 47 and a forehead band 49 are employed to ensure the patient's head is held securely and does not pivot relative to the brace.

Straps such as 43, 45, 47 and 49 are preferably made of a nylon web material while strap 41 is relatively larger and miry be made of leather. Clearly other strap materials are suitable. Each strap includes some sort of coupling arrangement for adjustably joining the free ends thereof. Straps 47 and 49 are joined by a hook and pile product such as VELCRO as at 51. Strap 41 is joinable by a conventional belt buckle 73. Shoulder straps 43 and 45 are joined by a quick release snap-fastening buckle of a type commonly found on sporting equipment, camera bags and the like. The two halves of buckle 87 are held to the shoulder pad 89 by tabs 91 and 93 so that releasing the buckle 87 provides additional slack in the strap 45, but does not completely free the ends. This aids the user in slipping an arm into the loop of strap 45. Strap 43 is similarly loosened, but not completely freed when buckle 95 is released. The shoulder pads such as 89 are wide leather shoulder pads and differ from the back padding 63, 65, etc. which are fabric covered resilient sponge material. A small strap (not shown) may be added to selectively connect the two shoulder straps 34 and 45 together and prevent their slipping apart and off the wearer's shoulders.

The uppermost one of the rigid members, headrest 85, differs from all the others and includes a pad 77 for engaging the patient's head as well as the chin 47 and forehead 49 straps, and is vertically adjustable. The headrest includes a pair of threaded rods 97 and 99 along which the padded portion 77 may be located by positioning the nuts 101, 103 and 105. Pivotable attachment of the headrest to the brace is by the resilient web 111 and threaded rod 113. When the nut 115 is tightened, the head rest pivots in the direction of the arrow. This tends to raise the chin and forehead of the wearer in the posterior direction and applies a bending moment to the superior end of the spinal column. Gradual adjustment over time assumes a more correct anatomical posture for all muscular, vascular and spinal column elements.

Extending across the shoulders is a plurality of generally transversely aligned rigid members such as 83, 107 and 109, each of which is pivotably coupled to an adjacent one for relative angular movement about a bending moment axis and that angular movement is selectively restricted in much the same manner as described previously. One of the two shoulder straps 43 is attached to a first end one 107 of the transversely aligned rigid members and the other 45 is attached to a second end one 109 of the transversely aligned rigid members.

Figure 2:
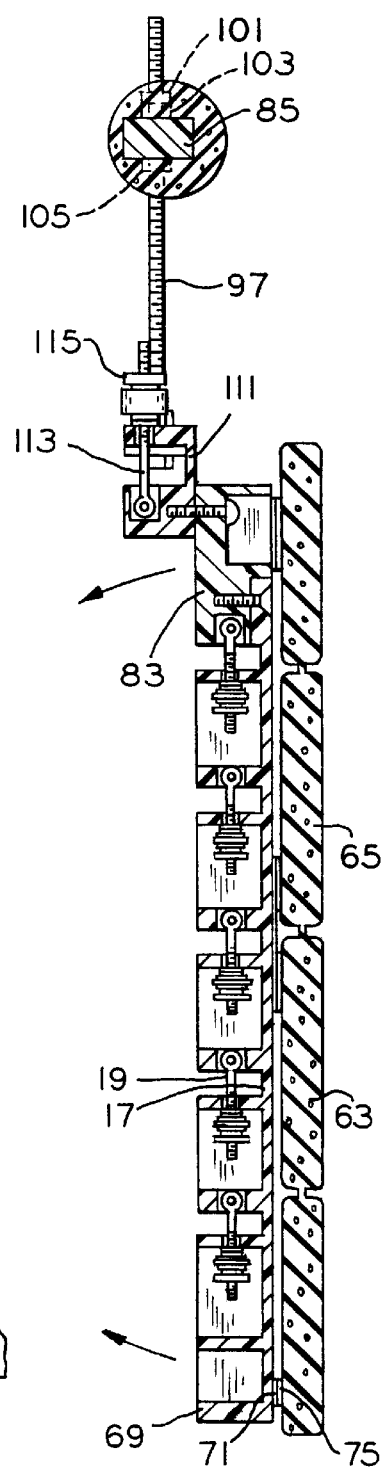
FIG. 2 is a side view in cross-section of the back brace along lines 2—2 of FIG. 1.

Mating strips of VELCRO 71 and 75 (FIG. 2) allow the resilient pads such as 63 and 65 to be removably affixed to the brace portions and to be interposed between the brace and a corresponding portion of the body such as the patient's hips or shoulders. The pads 63, 65, etc. may be portions of a single common removable padding as illustrated, or may be formed as individually removable segments if desired.

Figure 3:
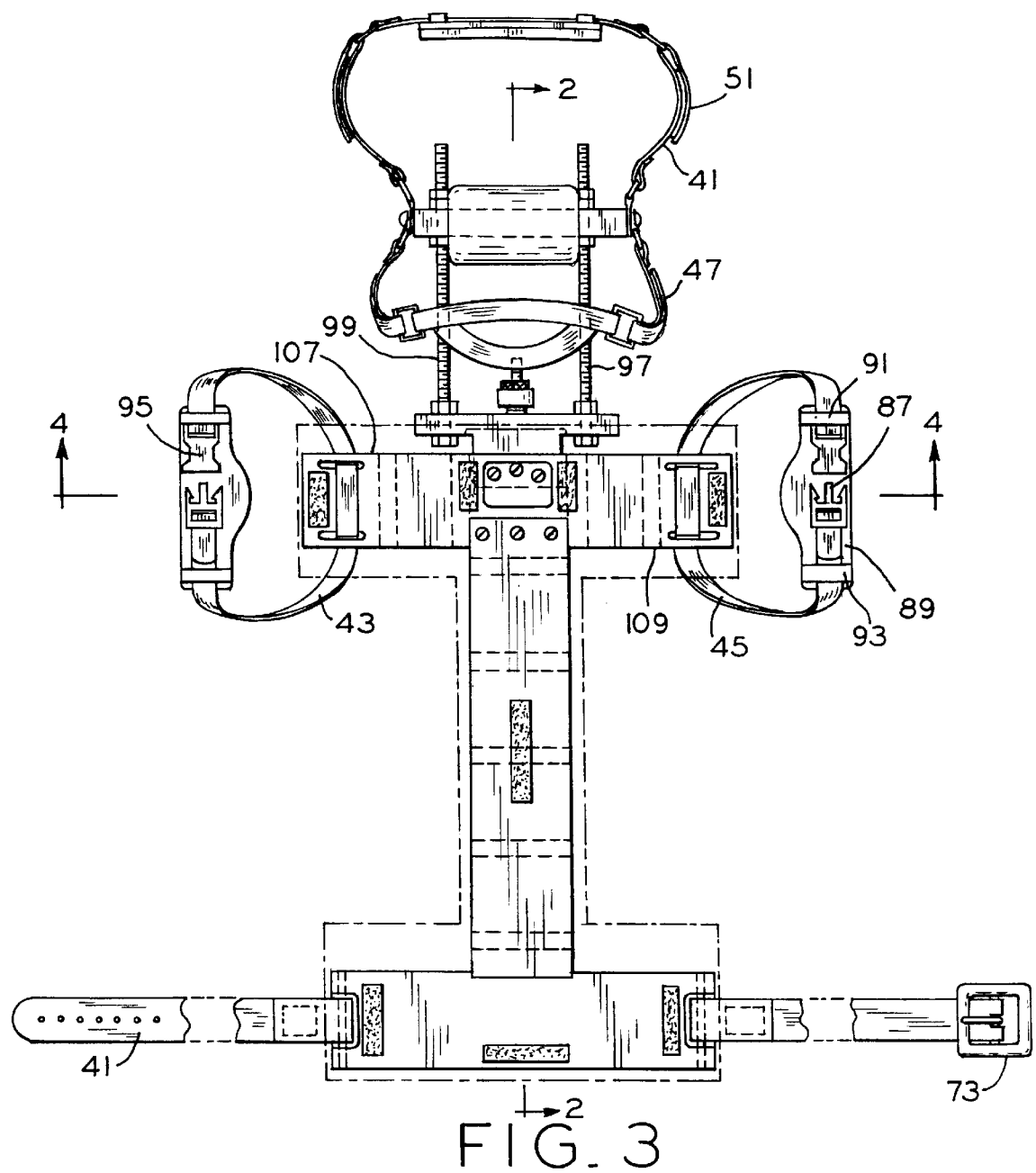
FIG. 3 is a back elevation view from the right side of FIG. 2.
Figure 4:
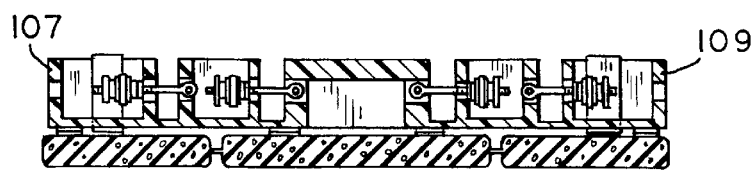
FIG. 4 is a cross-sectional view along lines 4—4 of FIG. 3.
Figure 5A:
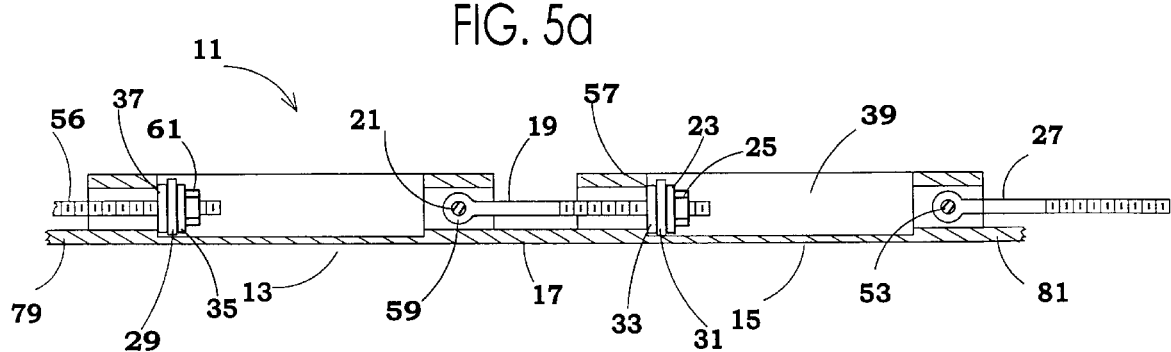
FIGS. 5a–5c are cross-sectional representations of an illustrative pair of articulated segments experiencing sequentially increasing angular displacement.
Figure 5B:
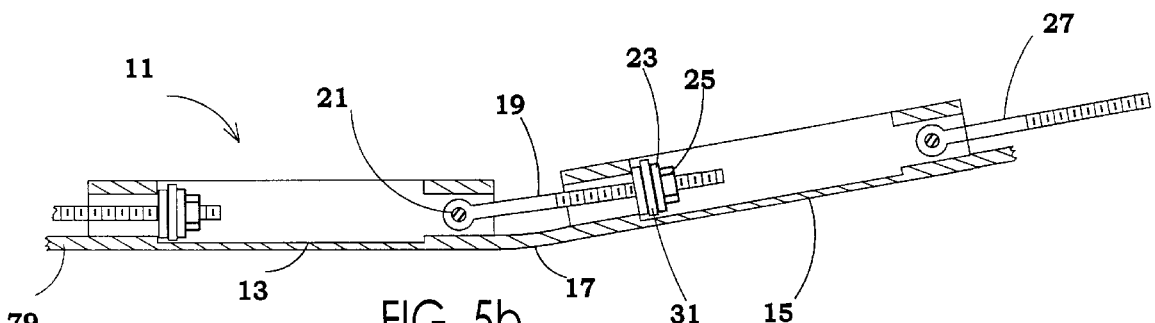
Figure 5C:
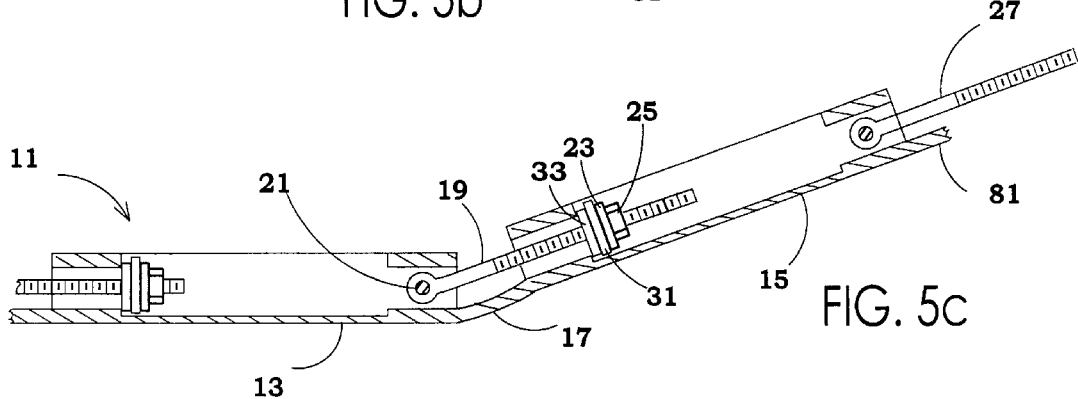

The basic components of the brace are rigid members, also called hollowed-out parallelepiped portions or segments. The sidewall portions such as 39 of each member provide structural support to help prevent distortion of the bottom or ends of the members. A two segment assembly 11 including rigid members such as 13 and 15 is shown in FIGS. 5a–5c. These members comprise hollowed-out rectangular parallelepipeds joined to an adjacent rigid member along adjacent generally parallel edges by a relatively thin web 17 of flexible material which is common to the two portions 13 and 15 to provide relative pivotal motion between the two portions as shown successively in FIGS. 5a, 5b and 5c. The angular relationship between adjacent segments is selectively restricted by an elongated threaded rod 19 which has an eye 59 which is pivotably affixed at one end to a transverse pin 21 of the rigid member 13 and extends through an end wall portion 57 of the other rigid member 15. Pin 21 may be held in position by a set screw or otherwise as desired. There is a washer 23 and a nut 25 threadedly engaging the rod 19. The nut is helically movable along the rod to selectively pull the rigid members 13 and 15 angularly toward each other. For some applications, the coupling between adjacent rigid members is too firm and a compressible rubber-like washer such as 29 may be positioned on the shaft 19 captive between the washers 35 and 37. Now some limited clockwise bending of the portion 15 and associated compression of the washer 29 can occur. Similarly, resilient washer 31 is shown captive between the metal washers 23 and 33 to provide limited yield between member 13 and rigid member 67. The pin 21 extends generally parallel to the axis of relative angular movement between the two members. The brace segments 13 and 15 normally assume the shape shown in FIG. 5a. When the nut 25 is tightened, the segments are drawn angularly toward each other against the natural resilience of the web 17. Note that the nut 25 is successively closer to the eye 59 as the two segments are pulled from their natural collinear relationship of FIG. 5a. While only two segments 13 and 15 are shown in FIGS. 5a–5c, it will be understood that the number of segments is somewhat arbitrary with six vertical segments or members shown in FIGS. 1, 2 and 3, and five transverse members shown in FIGS. 1, 2 and 4. Rod 27 is shown for angularly fixing the relationship between segment 15 and the lowermost hip segment 69. Similarly, the rod 56 and nut 61 are shown for angularly fixing the relationship between segment 13 and another segment 67 of FIGS. 1–3.

As an example, assume a human patient suffers from lordosis, an excessive posterior convexity of the spinal column. The brace may be utilized to apply corrective pressures or bending moments to selected spinal regions. Once the straps 41, 43, 45, and optionally, 47 and 49 have been coupled or tightened as by buckles such as 73, VELCRO strips 51 or the like, and the pivot axis 53 of pin 27 is aligned transversely with the wearer's lumbar region, nut 55 is threaded toward the pivot axis 53 imparting a straightening bending moment to the patient's lower back region. Similarly, tightening nut 25 imparts a corrective bending moment to the patient's back somewhat higher and tightening nut 61 applies this corrective bending moment even higher on the patient's back. These moments tend to cause the brace to bend concave outwardly in the direction of the arrows in FIG. 2 urging the central portion of the brace such as pads 63 and 65 against the wearer's back while exerting a tension primarily on the waist strap 41 and shoulder straps 43 and 45 and applying a bending moment to the spine in a direction tending to anatomically correct the lordosis. Clearly, similar bending moments may be applied to the neck or shoulders. While described as an orthopedic device, the brace may be used simply to immobilize a body part, for example, subsequent to an injury.

Numerous other brace configurations as well as numerous other applications should now be apparent. For example, a modification for treating scoliosis or for application where spinal contact is undesirable may be made by providing two spaced apart parallel independently adjustable vertical sections rather than the central column as shown.

From the foregoing, it is now apparent that a novel spinal orthosis has been disclosed meeting the objects and advantageous features set out hereinbefore as well as others, and that numerous modifications as to the precise shapes, configurations and details may be made by those having ordinary skill in the art without departing from the spirit of the invention or the scope thereof as set out by the claims which follow.

What is claimed is:

1. An externally applied non-invasive spinal column appliance adapted to span a plurality of vertebrae comprising:

a plurality of generally longitudinally aligned rigid members;

means pivotably coupling adjacent pairs of rigid members for relative angular movement about a bending moment axis;

means for selectively restricting the angular movement of each pivotably coupled pair about the bending moment axis including means engaging each of the adjacent rigid members for pulling the adjacent rigid members angularly toward one another; and strap means for encircling portions of a patient's body to secure the rigid members to the body and to transfer bending moment forces to the patient's spinal column.

2. The appliance of claim 1 wherein the strap means comprises at least two straps, one attached to a first end one of the rigid members and the other attached to a second end one of the rigid members, and each having coupling means for adjustably joining the free ends thereof, one of said straps adapted to encircle a patient's waist and the other adapted to encircle the patient's head.

3. The appliance of claim 2 wherein the second end one of the rigid members comprises a padded head rest vertically adjustably attached to an adjacent one of the rigid members.

4. The appliance of claim 3 wherein the padded head rest is adapted to engage the back of a patient's head and the strap encircles the patient's forehead, and further comprising a chin strap attached to the padded head rest and adapted to encircle the patient's head and chin.

5. The appliance of claim 1 further comprising a plurality of resilient pads, one affixed to each of the rigid members to be interposed between the rigid member and a corresponding body portion.

6. The appliance of claim 1 wherein each bending moment axis is generally parallel to every other bending moment axis.

7. The appliance of claim 1 wherein the means pivotably coupling comprises a relatively thin elongated web of flexible material common to the two rigid members.

8. The appliance of claim 7 wherein the rigid members comprise hollowed-out rectangular parallelepipeds joined to an adjacent rigid member along adjacent generally parallel edges.

9. The appliance of claim 1 wherein the means for selectively restricting includes an elongated threaded rod pivotably affixed at one end to one of the rigid members and extending through a portion of the other rigid member, and a nut threadedly engaging the rod and helically movable therealong to selectively pull the other member angularly toward the one rigid member.

10. The appliance of claim 9 wherein the rod has an eye near said one end and further comprising a pin passing through the eye and through a portion of said one rigid member generally parallel to said axis.

11. The appliance of claim 9 further including a resilient washer interposed between the nut and said portion of the other rigid member for reducing the rigidity of the restriction.

12. The appliance of claim 1 further including a plurality of generally transversely aligned rigid members;

means pivotably coupling adjacent pairs of the transversely aligned rigid members for relative angular movement about a bending moment axis; and means for selectively restricting the angular movement of each pivotably coupled transversely aligned pair about the bending moment axis including means engaging each of the adjacent rigid members for pulling the adjacent rigid members angularly toward one another.

13. The appliance of claim 12 further including at least two shoulder straps, one attached to a first end one of the transversely aligned rigid members and the other attached to a second end one of the transversely aligned rigid members, and each having coupling means for adjustably joining the free ends thereof, one of said straps adapted to encircle a patient's shoulder and the other adapted to encircle the patient's opposite shoulder.

14. The appliance of claim 13 further comprising an additional plurality of resilient pads, one affixed to each of the transversely aligned rigid members to be interposed between the rigid member and a corresponding body portion.

15. An orthopedic brace including at least two hollowed-out parallelepiped portions joined along a bending moment axis comprising a relatively thin web of flexible material common to the two portions to provide relative pivotal motion between the two portions, means for selectively restricting relative pivotal movement between the two portions including means engaging each of the two portions for pulling the two portions angularly about the bending moment axis toward each other, and a resilient coupling between said means and at least one of the portions for providing a limited pivotal yield between the two portions.

16. The orthopedic brace of claim 15 wherein the means for selectively restricting includes an elongated threaded rod pivotably affixed at one end to one of the parallelepiped portions and extending through a portion of the other parallelepiped portion, and a nut threadedly engaging the rod and helically movable therealong to selectively pull the other parallelepiped portion angularly toward the one parallelepiped portion; and the resilient coupling comprises a rubber-like washer interposed on the rod between the nut and said portion of the other parallelepiped portion.

17. The orthopedic brace of claim 16 wherein there are six longitudinally aligned parallelepiped portions each joined to another to form a pair by a relatively thin web and each pair having a threaded rod and nut for selectively restricting pivotal movement between the portions of the pair.

18. The orthopedic brace of claim 17 wherein there are five transversely aligned parallelepiped portions each joined to another to form a pair by a relatively thin web and each pair having a threaded rod and nut for selectively restricting pivotal movement between the portions of the pair, one said portion being common to both the transversely aligned and the longitudinally aligned parallelepiped portions.

19. An orthopedic appliance for posterior application to a human having a first plurality of longitudinally extending articulated segments positionable to extend generally along the human spine, adjacent pairs of the first plurality being pivotably joined for relative angular movement about a first set of pairwise parallel bending moment axes, and a second plurality of transversely extending articulated segments pivotably joined for relative angular movement about a second set of pairwise parallel bending moment axes extending generally orthogonal to said first set of bending moment axes.

20. The orthopedic appliance of claim 19 further comprising a waistband strap fastened to a lower end one of said first plurality of segments and adapted to encircle a human's waist, and a pair of shoulder straps fastened to an outermost pair of said second plurality of segments and adapted to encircle each of a human's arms near the torso.

21. The orthopedic appliance of claim 19 further comprising means associated with each axis for locking the adjoining segments in a preferred angular relationship to thereby apply a selectable bending moment to the human's back and shoulders.

22. The orthopedic appliance of claim 21 wherein one articulated segment is common to the first and second pluralities of articulated segments, and further comprising a padded head rest vertically adjustably attached to said one common segment for engaging the back of the human's head, a strap attached to the padded head rest and adapted to encircle the human's head near the forehead, and a second strap attached to the padded head rest and adapted to encircle the human's head near the chin.

* * * * *